United States Patent

Jäeger et al.

[11] Patent Number: 5,883,047
[45] Date of Patent: Mar. 16, 1999

[54] GRANULES OF HYGROSCOPIC, WATER-SOLUBLE PRODUCTS

[75] Inventors: Karl-Friedrich Jäeger; Hans-Michael Fricke, both of Limburgerhof, Germany

[73] Assignee: BASF Aktiengesellschaft, Ludwigshafen, Germany

[21] Appl. No.: 820,077

[22] Filed: Mar. 19, 1997

[30] Foreign Application Priority Data

Apr. 3, 1996 [DE] Germany .................. 196 13 395.5

[51] Int. Cl.$^6$ .................. A01N 25/12; C05G 5/00
[52] U.S. Cl. .................. 504/116; 71/64.03; 424/405; 514/951
[58] Field of Search .................. 504/116; 424/405; 514/951; 71/64.03

[56] References Cited

U.S. PATENT DOCUMENTS

| | | | |
|---|---|---|---|
| 4,015,970 | 4/1977 | Hennart | 71/11 |
| 4,936,901 | 6/1990 | Surgant, Sr. et al. | 71/92 |
| 5,516,521 | 5/1996 | Fersch et al. | 424/409 |

FOREIGN PATENT DOCUMENTS

| | | |
|---|---|---|
| 32 48 504 | 7/1983 | European Pat. Off. . |
| 0 388 867 | 9/1990 | European Pat. Off. . |
| 26 27 065 | 1/1977 | Germany . |

OTHER PUBLICATIONS

K.C. Lin et al, "Development of Solid Pesticide Formulations by Fluidized–Bed Technology", *ACS Symposium Series Pesticide Formulations*, Jan. 11, 1988, pp. 251–259, Series 371.

Michael Rosch et al, "Granulation in der Wirbelschicht", *Verfahrenstechnik*, 9, 1975, Nr. 2. pp. 59–64.

*Primary Examiner*—S. Mark Clardy
*Attorney, Agent, or Firm*—Oblon, Spivak, McClelland, Maier & Neustadt, P.C.

[57] ABSTRACT

The present invention relates to granules of water-soluble, hygroscopic products having a mean grain size in the range from 200 to 2000 μm, the granule grains consisting of an agglomerate of fine product particles having a mean particle size in the range from 5 to 200 μm, which are covered with a product layer.

21 Claims, 3 Drawing Sheets

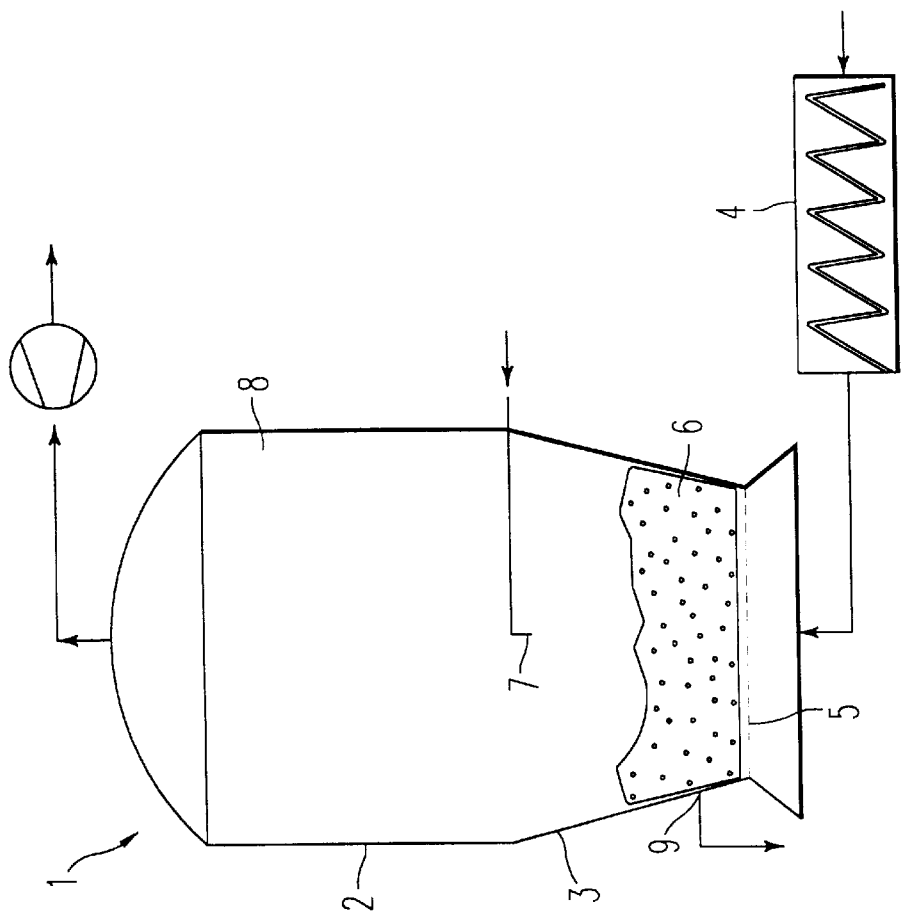
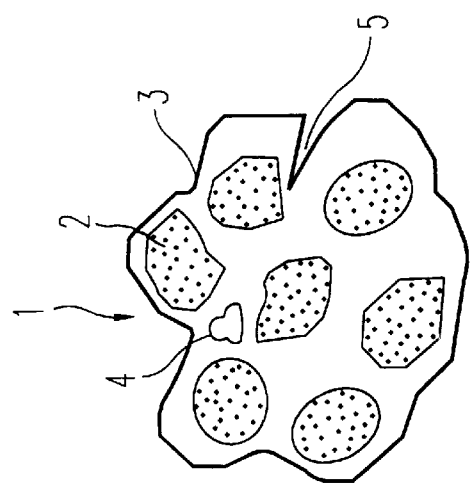
FIG. 4
FIG. 1
ABOUT 2000 μm

GRANULES OF HYGROSCOPIC, WATER-SOLUBLE PRODUCTS

The invention relates to granules of hygroscopic, water-soluble products, in particular products having biological action, such as drugs, crop treatment compositions, feeds and foodstuffs, and to a process for preparing the granules.

In the formulation of products having biological action, attention is also to be paid to product safety with regard to the user and the environment. Furthermore, no problems must occur during storage and transport, and the disposal of the product residues and the packaging must at least meet the current requirements.

In many areas, granules have proven to be the optimum form of formulation which fulfils the above requirements. Granules are usually low in dust and stable on storage and therefore offer high user safety. Additionally, they frequently have a relatively high bulk weight such that, in comparison to solutions, suspensions or powder formulations, less packaging material has to be used.

Granules can be prepared in a known manner, most expediently in a mixer, extruder, spray tower or in a fluidized bed. If the product to be granulated, however, is hygroscopic and tacky, problems occur. In a mixer or spray tower, highly concentrated granule formulations of the required quality and grain size cannot be prepared. On the contrary, finely divided powders are obtained which have a high dust content. Thus in these processes, only removal of the solvent occurs without granulation taking place. Because of the high tackiness of the moist powder compositions, it is not possible to carry out extruder processes.

U.S. Pat. No. 5,266,553 describes a process of this type, namely a process for preparing a water-soluble herbicide salt in dry, solid form, the water being removed from an aqueous solution of a salt of a herbicide at less than about 80° C. The removal of the water is carried out with the aid of customary apparatuses, namely a horizontally arranged, cylindrical dryer which works in a batchwise mode and is equipped with a plowshare attached to an axially rotating shaft and a radially arranged chopping tool. In this manner the herbicide salt, eg. the sodium salt of bentazone, is obtained in the form of a free-flowing, crystalline powder which dissolves completely and rapidly in cold water with formation of a clear solution. However, it has been shown that the product contains a high proportion of fine particles and therefore dusts severely.

Fluidized-bed granulation is a frequently used and well investigated method for preparing granules. For example, units and operating procedures for fluidized-bed granulation are described in Verfahrenstechnik [Process Technology] 9 (1975), 59–64. In a company publication of Glatt GmbH of 1986, Introduction to Fluid Bed Granulating, the product and process variables which have an influence on the granules to be obtained are investigated. None of these publications goes into the granulation of a hygroscopic, tacky product.

Despite all the investigations and knowledge about fluidized bed granulation, it was also not possible by this method until now to prepare granules of hygroscopic, tacky products. In conventional fluidized-bed granulation, a differentiation is made between, namely, a moist granulation phase and a drying phase. During the moist granulation phase, the water content in the fluidized bed increases and the granular particles are built up by the formation of liquid bridges with simultaneous drying. In the drying phase, the liquid bridges are completely dried and the granule structure is fixed. In the fluidized-bed granulation of hygroscopic, tacky products, this results in the formation of product particles whose surface is covered with a film of a saturated solution of the product to be granulated. This film determines the product behavior. Under normal operating conditions, on account of the tendency to agglutinate, large agglomerates are observed, such that the fluidized bed collapses or adequate drying of the product does not take place.

It is an object of the present invention to make available granules of hygroscopic, water-soluble products and a process for preparing these granules.

Surprisingly, we have found that this object is achieved if a fluidized-bed granulation is carried out under control of the product moistness of the granules.

The present invention therefore relates to granules of hygroscopic, water-soluble products having a mean grain size in the range from 200 to 2000 μm, the granule grains consisting of an agglomerate of fine product particles having a mean particle size in the range from 5 to 200 μm, which are covered with a layer of the product.

BRIEF DESCRIPTION OF THE DRAWINGS

The structure of the granule grains according to the invention is shown in FIGS. 1 to 3, where FIG. 1 is a schematic drawing of a granule grain according to the invention (sodium bentazone)

FIG. 4 is a graph of a fluidized-bed granulator useful for preparing the granules of the invention.

It can be inferred from FIG. 1 that a granule grain 1 comprises several particles 2 having a mean particle size in the range from 5 to 200 μm. These particles are connected to one another by means of solid bridges of solidified hygroscopic product, which cover a large part of the particle surface and if necessary can even form a matrix. The particles thus form an agglomerate which is covered with a layer 3 of the hygroscopic product (coating). The granule grains have an essentially round, compact form and exhibit capillary-active cavities 4 and pores 5. FIG. 2 shows this particularly clearly.

Figure 3:
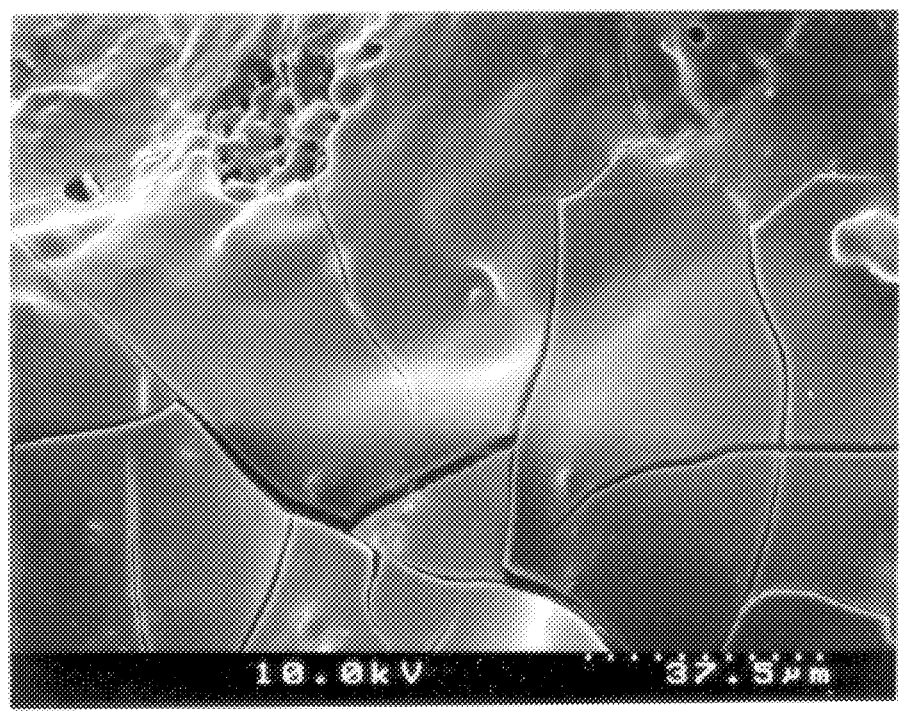
FIG. 3 is the photograph of a granule grain according to the invention (sodium bentazone) using a scanning electron microscope at 800-times magnification.

On account of the coating layer, the fine particles are well bound into the granules. Additionally, the coating layer rounds out the granule grain and provides for a compact, smooth outer surface, see FIG. 3. The granules are therefore particularly stable to abrasion. The binding of the fine fractions mentioned and the stability to abrasion have the result that the granules have only a very low dust content. The proportion of dust of <0.1 mm, determined according to Cipac MT170, "Trockensiebung von Granulaten" [Dry Screening of Granules] is <1%, in particular <0.5%.

The mean grain size of the granules is in the range from 200 to 2000 μm, preferably 500 to 1500 μm, at least 95% by weight of the granules having a grain size in the range from 0.1 mm to 3.0 mm.

On account of the grain size and the narrow grain size distribution, the granules are free-flowing. Additionally, the contact surfaces of the granules with one another are minimized. As a result, the tackiness and danger of caking of the granules on handling in moist air is minimized. Despite the hygroscopic constituents, the granules are thus easy and safe to meter in practice even in moist air.

The granules preferably have a bulk weight in the range from 300 to 800 g/l, in particular 400 to 800 g/l and preferably 600 to 800 g/l.

On account of the cavities and pores present in the granule grain, despite the compact coating layer a porosity adequate for rapid dissolution of the granules is retained. If the granules are introduced in a concentration of 0.5% by weight into water at 20° C. in a slowly rotating standing cylindrical vessel, they dissolve completely in less than 2 minutes and in particular less than 1 minute. A rapid, practically appropriate preparation of an aqueous solution or dispersion of the product is thus guaranteed.

The preparation of the granules according to the invention is explained below. For this purpose, customary apparatuses can be used for fluidized-bed granulation. A suitable apparatus is shown in FIG. 4, which is explained in greater detail in Example 1. The starting material used is an aqueous solution or dispersion of the hygroscopic, water-soluble (tacky) product, which in general contains from 20 to 70% by weight and in particular at least 40% by weight of the product. Beside water, the aqueous solution or dispersion can also contain organic solvents, for example alcohols, such as methanol, ethanol or glycol, ketones, such as acetone or methyl ethyl ketone, dimethylformamide or dimethyl sulfoxide. Preferably, however, the preparation is carried out in a purely aqueous solution or dispersion.

The aqueous solution or dispersion is subjected to fluidized-bed granulation, the aqueous solution or dispersion being sprayed onto the fluidized bed against the direction of flow of the heated fluidized gas, and the temperature and amount of the fluidized gas, the spray rate of the product and the concentration of the product in the aqueous solution or dispersion being selected such that the product moisture during the granulation is not more than approximately 50%, preferably not more than approximately 20%, higher than the residual moisture of the finished granules. Product moisture is in the present case understood as meaning the total product moisture, ie. the mean value of the moisture of the granules present at any time in the entire fluidized bed.

If the process is carried out under the conditions given above, it is no longer possible, as in conventional fluidized-bed granulation, to differentiate between the moist granulation phase and the drying phase. On the contrary, the process is operated near the final residual moisture of the product in the fluidized bed.

Preferably, the process is carried out at a product moisture of $\leq 6\%$ and in particular $\leq 2\%$.

The product moisture can be controlled by the interaction of temperature and amount of the fluidized gas, the spray rate of the product and the concentration of the product in the aqueous solution or dispersion. The process is in this case preferably carried out under the following conditions:

Inlet temperature of the fluidized gas: from 50° to 220° C., in particular from 70° to 200° C.

Amount of fluidized gas: from 10 to 500 and in particular from 50 to 300 m³/min per m² of incident flow area of the fluidized bed.

The spray rate and the concentration of the product in the aqueous solution or dispersion must in this case always be adapted to the particular conditions. The suitable values can be determined by means of a few routine tests.

It has further proven advantageous to work with a fluidized bed packing of from 50 to 2000 kg/m² of area of the incident flow base, preferably from 100 to 1000 kg/m². In the continuous procedure the "hold up" and in the batch process the batch size, ie. the amount of packing at the end of granulation, is meant by fluidized bed packing.

For spraying with nozzle of the aqueous solution or dispersion, one or more two-substance nozzles or three-substance nozzles are preferably used, which are operated using an inert gas, in general compressed air, at from 1.2 to 5.0 bar. The temperature of the compressed air is in general in the range from 15° to 100° C.

It has proven particularly advantageous to apply the nozzle at a distance from the incident flow base which corresponds to 1.5- to 10-times, in particular 2- to 8-times, the height of the layer of the resting fluidized bed packing. If the nozzle is too close above the fluidized bed or dips into the fluidized bed, severe agglomeration occurs and the fluidized bed collapses. If the distance of the nozzle from the fluidized bed is too large, the finely sprayed particles have time to begin drying, so that in general a powder and not granules, but at least a product having a high dust content, is obtained.

The process according to the invention can be carried out continuously or batchwise.

The residual moisture of the granules obtained is preferably $\leq 4\%$ by weight, in particular $\leq 2\%$ by weight and particularly preferably $\leq 1\%$ by weight.

Beside the hygroscopic product, the aqueous solution or dispersion to be sprayed into the fluidized bed can, if desired, also contain inert filling materials, wetting agents and dispersants, binders and/or additives, such as preservatives and colorants.

Suitable inert filling materials are customarily used fillers and carriers, for example inorganic salts, such as alkali metal, magnesium and ammonium chlorides and sulfates, in particular magnesium sulfate, potassium sulfate, sodium sulfate, potassium chloride, ammonium sulfate, lithium sulfate and ammonium chloride, as well as oxides, for example magnesium oxide, nitrates, carbonates, hydrogen carbonates, silicates, talc, chalk, quartz powder, kaolin, and also urea and urea derivatives, such as hexamethylenetetramine, carbohydrates, such as starch, sugar, alginates and their derivatives, cereal flours such as wheat flour and rice flour and finally water-soluble polymers, such as polyvinyl alcohol and polyvinylpyrrolidone.

Suitable wetting agents and dispersants are anionic or cationic, amphoteric or nonionic surface-active substances, in particular anionic wetting agents, such as condensation products of aromatic sulfonic acids and formaldehyde, lignosulfonic acid salts, such as sodium, potassium and ammonium salts of lignosulfonic acid, alkylsulfonates as well as polyoxyethylene fatty acid esters, polyoxyethylene fatty alcohol ethers, etc.

Suitable binders (adhesives) are, in particular, polyvinylpyrrolidone, polyvinyl alcohol and polyvinyl acetate.

Examples of suitable preservatives are 2-hydroxybiphenyl, sorbic acid, p-hydroxybenzaldehyde, methyl p-hydroxybenzoate, propyl p-hydroxybenzoate and benzoic acid.

Examples of suitable colorants are inorganic pigments such as iron oxide, titanium dioxide and Prussian Blue and organic dyes, such as alizarin, azo and metal phthalocyanine dyes.

Granulation can be carried out in air or inert gases, such as nitrogen. Granulation can be started in the empty fluidized bed apparatus, finely divided material first being produced as granulation cores. Granulation cores of this type, however, can also be added to the fluidized bed apparatus, for example a powder of the product to be granulated or the abovementioned inert materials. It is also possible to start the granulation in a fluidized bed apparatus in which starter granules are already contained.

The fine material fractions escaping with the off-gas from the fluidized bed are deposited in the customary manner; they can be fed back into the fluidized bed as seeds for granule formation. In this case, both internal and external recycling of fine material is possible. For the deposition of the fine material fractions and their recycling, all apparatuses customarily employed for purposes of this type can be used.

The finished granules are discharged by means of one or more suitable apparatuses. Those suitable for this purpose are all customary apparatuses, for example countercurrent gravity sifters, zigzag sifters or discharge via a valve.

According to the invention, granules of all hygroscopic, water-soluble and tacky products can be prepared. The granules according to the invention are in particular of importance in products having biological action, such as drugs, including veterinary drugs, fertilizers, feeds, foodstuffs and preferably crop treatment compositions such as crop protection compositions.

The hygroscopic product is particularly preferably a crop protection composition, and in particular bentazone salts, such as sodium- or potassium-bentazone, salts of 2-methyl-4-chloro-phenoxyacetic acid (MCPA), salts of 2-(2-methyl-4-chlorophenoxy)-propionic acid (MCPP), 2-methyl-4-chlorophenoxybutyric acid (MCPB), 2,4-dichlorophenoxyacetic acid (2,4-D), 2-(2,4-dichlorophenoxy)propionic acid (2,4-DP) and 2,4-dichlorophenoxybutyric acid (2,4-PB). These salts are in particular the alkali metal salts, such as the sodium or potassium salts, or the ammonium salts including the substituted ammonium salts, such as hydroxy-alkylammonium salt, dihydroxyalkylammonium salt, alkylammonium salt, dialkylammonium salt or trialkylammonium salt.

Further preferred hygroscopic products are mepiquat chloride of the formula

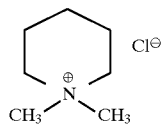

and chlormequat chloride of the formula

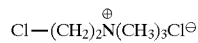

Granules of hygroscopic cyclohexenone herbicides can furthermore be prepared. Examples of herbicides of this type are sethoxydim, cycloxydim, 2-(1-(3-chloroallyloxy) iminopropyl)-5-(tetrahydropyran-4-yl)-3-hydroxycyclohex-2-enone or mixtures thereof.

Granules of the sodium or potassium salts of acifluorfen can also be prepared.

The granules according to the invention in general contain the hygroscopic product in an amount from 40 to 100% by weight and in particular from 60 to 100% by weight.

The present invention also relates to compositions which comprise the granules according to the invention. These compositions can also contain customary formulation substances and additives as well as other active ingredients. For example, beside a crop protection agent, the compositions according to the invention can also contain fertilizers, such as ammonium sulfate or ureas, growth regulators, other crop protection agents, pesticides, etc.

Suitable formulation agents and additives are customary products which are necessary for the applicational properties and the optimum biological action of the active ingredients. Examples of formulation auxiliaries and additives of this type are anticaking agents, flow auxiliaries, etc.

Preferably, however, the granules according to the invention are used without auxiliaries and additives.

The following examples explain the invention without restricting it.

The granules described in the examples were prepared in a fluidized bed apparatus of the type shown in FIG. 4. This is a customary fluidized-bed granulator 1, which comprises a cylindrical section 2 and a conical section 3. The fluidized gas used was air, which was heated in the heat exchanger 4 and passed through the incident flow base 5 into the fluidized bed 6. The product to be granulated was sprayed onto the fluidized bed 6 in the form of an aqueous solution by means of a two-substance nozzle 7. The fine material fraction was separated off by the tube filters 8 attached above the two-substance nozzle 7 and washed back from time to time with compressed air. The waste air leaving the fluidized-bed granulator was recirculated via the heat exchanger 4. The granules obtained were discharged via a discharge valve 9.

EXAMPLE 1

Preparation of Sodium Bentazone Granules 190 g of powdered ammonium sulfate were initially introduced into a laboratory fluidized-bed granulator of the type shown in FIG. 4 and fluidized at a feed air temperature of 120° C. with a feed air quantity of 32 m³/h. 16 cm above the fluidized-bed base was a two-substance nozzle. The fluidized-bed base had an incident flow area of 153 cm².

414 g of powdered sodium bentazone were dissolved in 300 g of water. This solution was sprayed into the fluidized bed for 100 minutes and dried. The two-substance nozzle was operated at a compressed air pressure of 2 bar. After completion of the spraying-in, the heating was turned off and fluidization was carried out for 1 minute further. The unit was then switched off and the product was removed. At the end of the experiment, the product in the fluidized bed had a bed height of 6 cm above the fluidizing base in the resting state.

Figure 2:
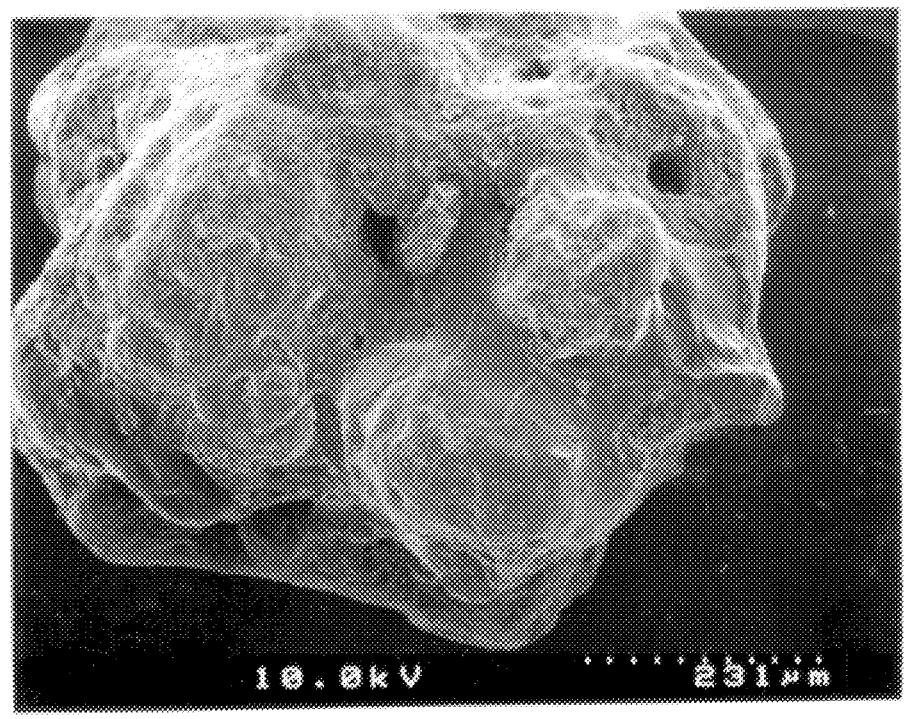
FIG. 2 is the photograph of a granule grain according to the invention (sodium bentazone) using a scanning electron microscope at 130-times magnification.

The product contained 68.9% of sodium bentazone and had a residual moisture of 0.9%. The granules had round, compact agglomerate structures of the type shown in FIGS. 1 to 3. The mean grain size was 0.36 mm. The product was almost dust-free. The fine fraction in the product was 0.1% less than 0.1 mm. The bulk weight had a value of 741 g/l. The granules dissolved completely within 1 minute at a concentration of 0.5% in water at 20° C. in a standing cylindrical vessel which was slowly rotated. The product was free-flowing.

EXAMPLE 2

Continuous Granulation of Sodium Bentazone 79 kg of sodium bentazone granules containing 99% sodium bentazone and 1% residual moisture were packed into an Institute of Technology fluidized-bed granulating unit of the type shown in FIG. 4. The fluidizing base of the unit had an incident flow area of 0.26 m². Above the fluidizing base was situated a two-substances nozzle at a distance of 140 cm. A feed air quantity of 3000 kg of air/h was sucked through the unit with an inlet temperature of 140° C. The aqueous sodium bentazone solution was sprayed into the fluidized granule layer via the two-substance nozzle in a concentration of 55% at a spray rate of 100 kg/h. This corresponds to a sprayed-in water quantity of 45 kg/h. Atomization through the two-substance nozzle was carried out using 100 kg/h of nozzle gas. The product was continuously discharged through a valve in the vicinity of the sieve base at a rate of 55 kg/h. In the resting state, the bed height of the product was 31.5 cm relative to the fluidizing base. The granules discharged contained 99% of sodium bentazone and had a residual moisture of 1%. The mean granule grain size was 0.5 mm; fine fractions <0.1 mm were not present. The bulk weight had a value of 709 g/l. The granules were dust-free and stable to abrasion. In an abrasion test, the product was stressed in a glass bottle at a speed of rotation of 76 rpm for 3 hours in a tumble mixer. In this process, 0.7% abraded material having a grain size of less than 0.05 mm resulted. The granule structure was a round, compact agglomerate. The granules dissolved completely at a concentration of 0.5% in water at 10° C. within 1 minute in a standing cylindrical vessel which slowly rotated. The product was free-flowing.

EXAMPLE 3

Preparation of Mepiquat Chloride Granules 221 g of sodium lignosulfonate were mixed in 3.5 kg of an aqueous solution of mepiquat chloride (concentration 57% mepiquat chloride).

The solution was then sprayed through a nozzle into a laboratory fluidized-bed granulator of the type shown in FIG. 4 at an air inlet temperature of 130° C. by means of a two-substance nozzle for 115 minutes. The area of the incident flow base was 221 cm². The nozzle was 34 cm above the incident flow base. The nozzle was operated using compressed air at 2 bar. The feed air quantity was 120 m³/h. With simultaneous drying, the product granulated during the spraying-in operation. After completion of spraying-in, the heating was turned off and the product was fluidized further for 1 minute to cool it. After turning off the unit, the product in the fluidizing container in the resting state had a bed height of 17 cm above the fluidizing base.

The product contained 90% mepiquat chloride and had a residual moisture of 0.2%. The granules had compact agglomerate structures of tile type shown in FIGS. 1 to 3. The mean grain size was 0.65 mm. The product was dust-free; no fine fraction of less than 0.1 mm was present. The bulk weight had a value of 400 g/l. The granules dissolved completely within 30 seconds in water at 10° C. in a concentration of 0.5% in a standing cylindrical vessel (250 ml) which was slowly rotated. The product was free-flowing.

EXAMPLE 4

Preparation of Chlormequat Chloride Granules

A solution of 300 g of sodium naphthalene-2-sulfo acid-formaldehyde condensate in 430 g of water was mixed in 4.188 kg of an aqueous solution of chlormequat chloride (concentration 69% chlormequat chloride). This solution was then sprayed through a nozzle for 170 minutes into a laboratory fluidized-bed granulator of the type shown in FIG. 4 by means of a two-substance nozzle. The area of the incident flow base was 221 cm². The nozzle was 34 cm above the incident flow base and was operated using compressed air at 2 bar. The feed air quantity was 120 m³/h; the feed air temperature was 130° C. With simultaneous drying, the product granulated during the spraying-in operation. After completion of spraying-in, the heating was turned off and the product was further fluidized for 1 minute to cool it. After turning off the unit, the product in the fluidizing container in the resting state had a bed height of 22 cm above the incident flow base.

The product contained 90% chlormequat chloride and had a residual moisture of 0.7%. The granules had compact agglomerate structures of the type shown in FIGS. 1 to 3. The mean grain size was 0.5 mm. The product was almost dust-free; 0.03% fine fractions of less than 0.10 mm were present. The bulk weight had a value of 468 g/l. The granules dissolved completely in water at 10° C. in a concentration of 0.5% within 30 seconds in a slowly rotated standing cylindrical vessel (250 ml) The product was free-flowing.

EXAMPLE 5

Preparation of Potassium Mecoprop (MCPP) Granules 4 kg of potassium mecoprop solution (58.4% potassium mecoprop) were sprayed through a nozzle for 117 minutes into a laboratory fluidized-bed granulator of the type shown in FIG. 4 by means of a two-substance nozzle. The area of the incident flow base was 221 cm². The nozzle was 34 cm above the fluidizing base and was operated using compressed air at 2 bar. The feed air quantity was 120 m³/h; the feed air temperature was 130° C. On simultaneous drying, the product granulated during the spraying-in operation After completion of spraying-in, the heating was turned off and the product was further fluidized for 1 minute to cool it. After turning off the unit, the product in the fluidizing container in the resting state had a bed height of 16 cm above the incident flow base.

The product contained 99.9% potassium mecoprop and had a residual moisture of 0.1%. The granules consisted of compact agglomerate structures of the type shown in FIGS. 1 to 3. The mean grain size was 0.5 mm. The granules were dust-free. No fractions of less than 0.16 mm were present in the product. The bulk weight. had a value of 460 g/l. The granules dissolved completely in water at 10° C. in a concentration of 0.5% within 1 minute in a slowly rotated standing cylindrical vessel (250 ml). The product was free-flowing.

Comparison Example 1

Spray drying of sodium bentazone using a two-substance nozzle

A 55% aqueous solution of sodium bentazone was sprayed into an Institute of Technology spray tower by means of a two-substance nozzle and dried. The tower inlet temperature of the drying air was 170° C., the tower outlet temperature 90° C. The two-substance nozzle was operated at a spray pressure of 2 bar. The air throughput through the spray tower was 360 m³/h, the spray rate of liquid 16 l/h.

A fine sodium bentazone powder containing 2.0% residual moisture was obtained in the downstream cyclone. The powder had a bulk weight of 673 g/l. The grain size of the product was 100% less than 0.1 mm. The product dusted severely.

This experiment shows that a severely dusting product is obtained- No granules were formed.

Comparison Example 2
Drying of sodium bentazone in a vacuum mixer 70 kg of aqueous sodium bentazone solution (56% w/w) were dispensed into a batch vacuum mixer (Littleford) of 130 l volume. The mixer had a heatable, cylindrical container. In the inside of the mixer was axially arranged a rotating mixer with plowshares. A chopping tool which could be rotated at high speeds of rotation was attached to the container wall. The mixer was operated under vacuum at 60° C. until 30.7 kg of water were evaporated. A product having a residual water content of 0.4% and a bulk weight of 0.7 kg/l was obtained. The product contained a large powder fraction (30% less than 0.15 mm) and exhibited severe dusting.

This experiment was carried out essentially similarly to Example 8 of U.S. Pat. No. 5,266,553. It is evident that no granules, but a severely dusting product, was obtained.

Comparison Example 3
Granulation experiment in a vortex mixer 4125 g of sodium bentazone powder from Comparison Example 1 were mixed in a laboratory vortex mixer (PK-Niro) having a chopper shaft and integrated liquid metering device. The mixer ran at a speed of rotation of 60 rpm. The chopper shaft was operated at a speed of rotation of 1100 rpm. 768 g of aqueous sodium bentazones solution (56% w/w) were slowly introduced via the chopper shaft. Moist granules could not be detected during this introduction process. Energy is introduced by means of the chopper shaft. At a temperature of 43° C., a sharp transition from moist, nongranulated powder to a viscous material resulted at the end of the introduction of liquid. Granules could not be prepared.

We claim:

1. A granule of water-soluble, hygroscopic product, consisting of:
   fine hygroscopic product particles having a mean particle size in the range from 5–200 μm covered with a layer of hygroscopic product resulting in granules of hygroscopic product ranging in size from 200–2,000 μm.

2. A granule as claimed in claim 1, wherein the mean grain size is in the range from 500 to 1500 μm.

3. A granule as claimed in claim 1 or 2, which has a bulk weight in the range from 300 to 800 g/l.

4. A granule as claimed in claim 1, which dissolves in water at 20° C. in less than 2 minutes at a concentration of 0.5% by weight.

5. A granule as claimed in claim 1, wherein the residual moisture is $\leq 4\%$ by weight.

6. A granule as claimed in claim 5, wherein said residual moisture content is $\leq 2\%$ by weight.

7. A granule as claimed in claim 1, the hygroscopic product being a crop protection active compound which is selected from the group consisting of bentazone salts, salts of 2,4-dichlorophenoxyacetic acid, 2-(2,4-dichlorophenoxy)-propionic acid, 2,4-dichlorophenoxybutyric acid, 2-methyl-4-chlorophenoxyacetic acid, 2-(2-methyl-4-chlorophenoxypropionic acid, and 2-methyl-4-chlorophenoxybutyric acid, mepiquat salts, chlormequat salts, sethoxydim, cycloxydim, tepraloxydim and salts of acifluorfen.

8. A granule as claimed in claim 7, wherein said mepiquat salt is mepiquat chloride and said chlormequat salt is chlormequat chloride.

9. A granule as claimed in claim 7, wherein the crop protection active compound is sodium or potassium bentazone.

10. A granule as claimed in claim 9, wherein the bulk weight is at least 600 g/l.

11. A granule as claimed in claim 1, wherein the agglomerate comprises particles of an inert material or of another product having biological action.

12. A granule as claimed in claim 1, wherein the proportion of the hygroscopic product in the granule is in the range from 20 to 100% by weight.

13. A composition comprising granules of the water-soluble hygroscopic granule product of claim 1, and at least one member selected from the group consisting of formulating substances, additives and active ingredients.

14. The composition as claimed in claim 13, wherein said active ingredient is fertilizers, plant growth regulators, other crop protection agents and pesticides.

15. A granule of water-soluble, hygroscopic product, consisting of:
   fine hygroscopic product combined with at least one material selected from the group consisting of wetting agents, dispersants and binders as particles having a mean particle size in the range from 5–200 μm joined together and covered with a layer of hygroscopic product combined with at least one material selected from the group consisting of wetting agents, dispersants and binders resulting in granule product ranging in size from 200–2,000 m.

16. A process for preparing the granule as claimed in claim 1, which comprises:
   subjecting an aqueous solution or dispersion of the hygroscopic product, optionally containing a wetting agent, dispersant, binder or combination thereof, to fluidized-bed granulation by spraying the aqueous solution or dispersion through a nozzle onto the fluidized bed against the direction of flow of a heated fluidized gas passed through the fluidized bed, the temperature and the amount of fluidized gas, the spray rate of the hygroscopic product and the concentration of the hygroscopic product in the aqueous solution or dispersion being selected such that the product moisture during granulation is not more than approximately 50% higher than the residual moisture of the finished granules.

17. A process as claimed in claim 16, wherein the product moisture is $\leq 6\%$ by weight.

18. A process as claimed in claim 17, wherein the product moisture is $\leq 2\%$ by weight.

19. A process as claimed in claim 16 or 17, wherein the temperature of the fluidized gas is in the range from 50 to 220° C.

20. A process as claimed in claim 16, wherein the fluidized gas amount is from 10 to 500 $m^3$/min per $m^2$ of incident flow area of the fluidizing base.

21. A process as claimed in claim 16, wherein the distance of the nozzle from which the aqueous solution or dispersion of the hygroscopic product is sprayed onto the fluidized bed is 1.5- to 10-times the height of the layer of the resting fluidized bed packing.

* * * * *